(12) United States Patent
Travassos et al.

(10) Patent No.: US 6,682,900 B1
(45) Date of Patent: Jan. 27, 2004

(54) SEROLOGICAL DIAGNOSIS OF CHAGAS' DISEASE

(75) Inventors: Luiz R. R. G. Travassos, São Paulo (BR); Igor C. Almeida, São Paulo (BR); Dimas Tadeu Covas, Ribeirão Preto (BR)

(73) Assignee: Fundação Hemocentro de Ribeirão Preto, Ribeirão Preto (BR)

( * ) Notice: Subject to any disclaimer, the term of this patent is extended or adjusted under 35 U.S.C. 154(b) by 0 days.

(21) Appl. No.: 09/554,312

(22) PCT Filed: Feb. 16, 1998

(86) PCT No.: PCT/BR98/00006

§ 371 (c)(1),
(2), (4) Date: Sep. 21, 2000

(87) PCT Pub. No.: WO99/41610

PCT Pub. Date: Aug. 19, 1999

(30) Foreign Application Priority Data

Aug. 2, 1996 (BR) .............................................. 9603267

(51) Int. Cl.$^7$ ...................... G01N 33/53; G01N 33/569; C12N 1/10; A61K 39/00; A61K 39/002
(52) U.S. Cl. .................. 435/7.22; 435/7.1; 435/947; 429/184.1; 429/265.1; 429/269.1
(58) Field of Search ........................... 424/265.1, 269.1, 424/184.1; 435/7.1, 947, 7.22

(56) References Cited

U.S. PATENT DOCUMENTS

| | | | | |
|---|---|---|---|---|
| 3,993,743 A | * | 11/1976 | Hanson | ........................ 424/12 |
| 4,870,006 A | * | 9/1989 | Dragon et al. | .................. 435/7 |
| 5,234,822 A | * | 8/1993 | Pereira et al. | .............. 435/69.1 |

FOREIGN PATENT DOCUMENTS

| | | | | |
|---|---|---|---|---|
| BR | 9400950-3 A | * | 7/1995 | ......... G01N/33/569 |
| WO | WO 92/09895 | * | 6/1992 | ......... G01N/33/569 |
| WO | WO 97/05468 | * | 2/1997 | ......... G01N/33/569 |

OTHER PUBLICATIONS

Almeida, I.C. et al. "A highly sensitive and specific chemiluminescent enzyme–linked immunosorbent assay for diagnosis of active *Trypanosoma cruzi infection*", Tranfusion, vol. 37, pp. 850–857, 1997.*

Grijalva,M.J. et al. "Blood donors in a vector–free zone of Ecuadopr potentially infected with *Trypanosoma cruzi*". American Journal of Tropical Medicine and Hygiene, vol. 52, No. 4, pp. 360–363, 1995.*

Almeida, I.C. et al. "Lytic anti–alpha–galactolsyl antibodies from patients with chronic Chagas'disease . . . " Biochemical Journal, vol. 304, pp. 793–802, 1994.*

Bates et al. , "Leishmania mexicana: Induction of Metacyclogensis by cCultivation", Experimental Parasitology vol. 76, pp.412–423, 1993.*

Almeida, I.C. et al. "A highly sensitive and specific chemiluminescent enzyme–linked immunosorbent assay for diagnosis of active *Trypanosoma cruzi*infection", Tranfusion, vol. 37, pp. 850–857, 1997.*

Grijalva,M.J. et al. "Blood donors in a vector–free zone of Ecuadopr potentially infected with *Trypanosoma cruzi*". American Journal of Tropical Medicine and Hygiene, vol. 52, No. 4, pp. 360–363, 1995.*

Almeida, I.C. et al. "Lytic anti–alpha–galactolsyl antibodies from patients with chronic Chagas'disease . . . " Biochemical Journal, vol. 304, pp. 793–802, 1994.*

Biological Abstracts, XP00203817, vol. 97 (1997).

* cited by examiner

*Primary Examiner*—Rodney P Swartz
*Assistant Examiner*—Khatol S. Shahnan-Shah
(74) *Attorney, Agent, or Firm*—Birch, Stewart, Kolasch & Birch, LLP

(57) ABSTRACT

A chemiluminescent (CL)-ELISA method with purified and complex antigens of *Trypanosoma cruzi* is proposed for the specific and sensitive diagnosis of Chagas' disease in patients and blood bank samples. A trypomastigote specific antigen (A&T) together with an epimastigote extract (EpEx), used as a control of sensitivity, are the preparations used. The high sensitivity of the CL-ELISA method permits the use of extremely small amounts of antigen and allows a serum dilution in routine tests as high as 1:2000, thus reducing the nonspecific or false-positive reactions to a minimum. The use of the A&T purified antigen eliminates cross-reactivities with other infectious agents, detects active infection, and serves to monitor chemotherapy in chronic patients. The use of the EpEx antigenic preparation not only confirms the positive results with A&T but also, in case of discrepancy, suggests other infections such as leishmaniasis. In comparison with current tests used in major blood banks, the CL-ELISA method with A&T and EpEx antigens, tested in parallel, proved to be clearly superior either by eliminating indeterminate results or by increasing the statistics of diagnosed positive samples.

2 Claims, 2 Drawing Sheets

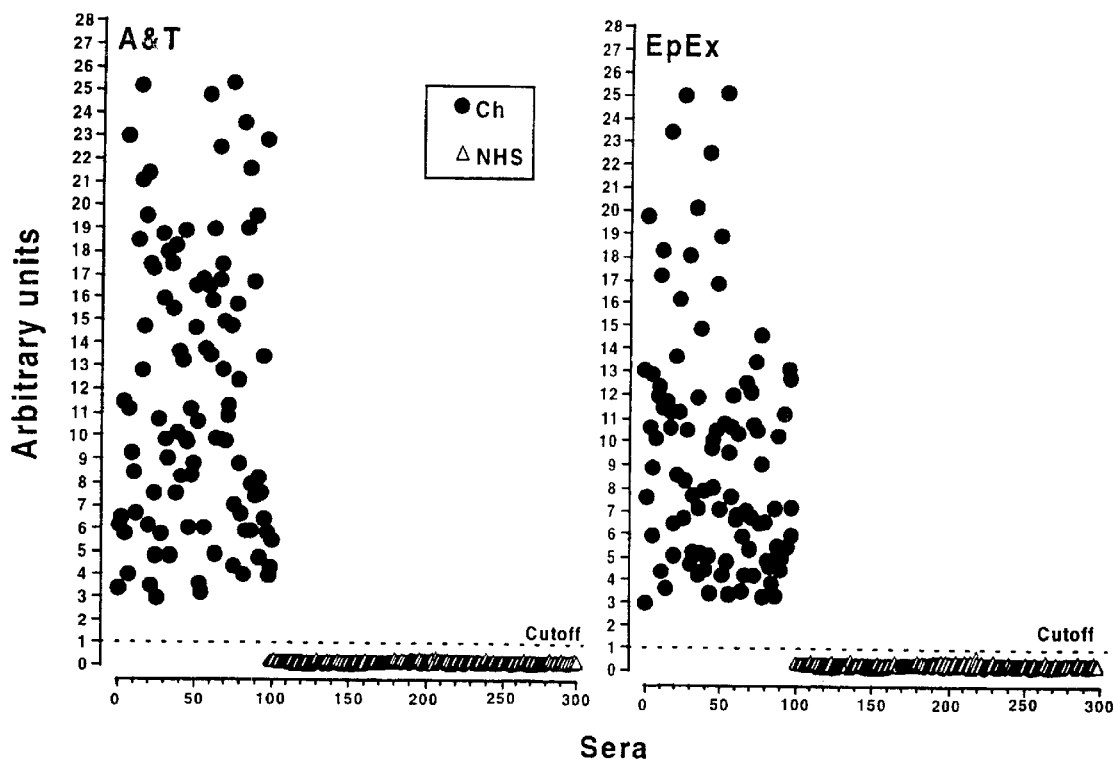
Fig. 1. Evaluation of the sensitivity of CL - ELISAs using A&T and EpEx antigens. Ch, chronic Chagasic sera (n=100); NHS, normal human sera (n=200).

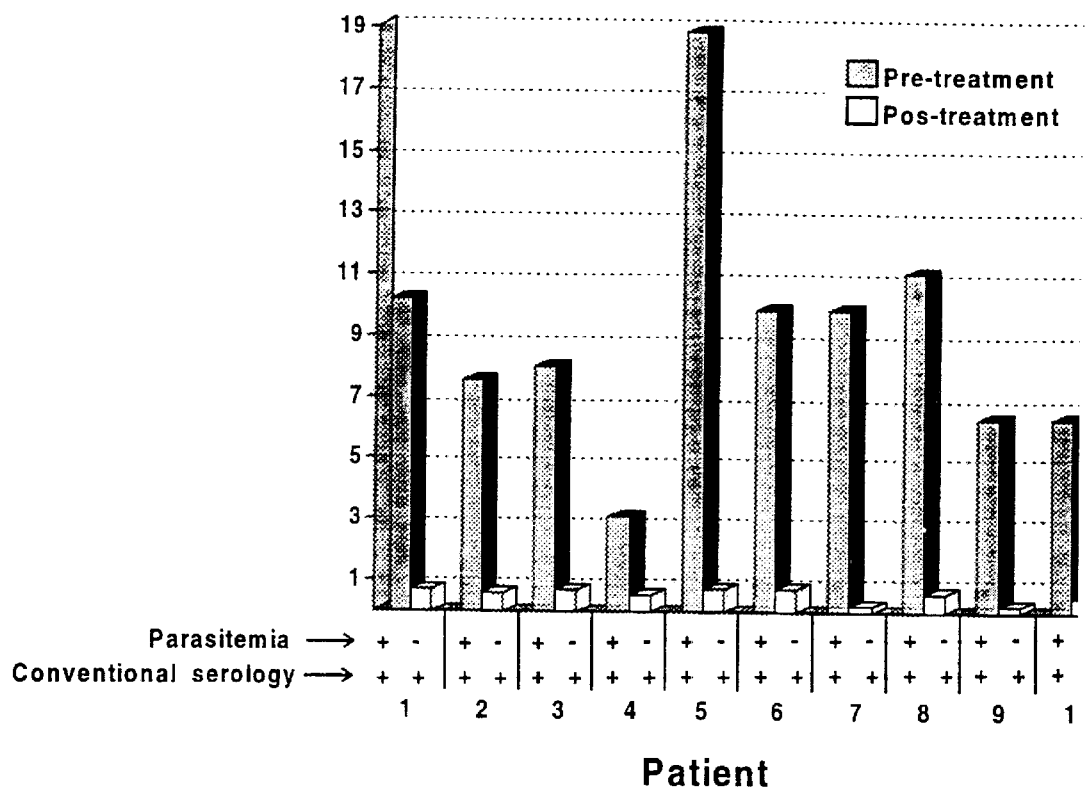
Fig. 2 - CL-ELISA using A&T antigen as a criterion of cure of treated Cha patients. Parasitemia was estimated by xenodiagnosis or hemocul Conventional serology: indiret hemagglutination, indirect immunofluorescence and Elisa.

SEROLOGICAL DIAGNOSIS OF CHAGAS' DISEASE

This application is the national phase under 35 U.S.C. §371 of PCT International Application No. PCT/BR98/00006 which has an International filing date of Feb. 16, 1998, which designated the United States of America.

BACKGROUND OF THE INVENTION

Chagas' disease is characterized by a short-term acute phase, with very few clinical symptoms, and a long-term chronic phase, usually accompanied by severe gastrointestinal and/or cardic complications which result in permanent physical disability or death.

Chagas' disease is an endemic disease caused by the flagellate *Trypanosoma cruzi*. In Latin America, approximately 16 to 18 million individuals are already infected and as many as 90 million individuals are at risk of infection (W.H.O., 1991). The disease is transmitted in Nature by Triatominae vectors. As a result of effective public health measures for the control of the vector in most countries, blood transfusion is quantitatively the most important form of transmission of the disease today. In Latin America, blood samples with antibodies associated with Chagas' disease represent 1–4% of the total blood samples in major Hemocenters. More recently, Chagas' disease has also become a major public health concern in North America, owing to the increasing number of immigrants from Latin American countries, in the last decade. Recent studies estimate that there may be in the United States approximately 100,000 *Trypanosoma cruzi*-infected individuals with potential risk of transmitting Chagas' disease by blood transfusion (Hagar and Rahimtoola, 1991).

The diagnosis of acute Chagas' disease is not a problem because of the large number of parasites in the blood. In contrast, the chronic phase is diagnosed by serological methods because of the very small number or absence of circulating parasites. This has also restricted so far the use of polymerase chain reaction (PCR) with specific primers, as the final diagnostic test of Chagas' disease, before a major epidemiologic survey of sera from chronic patients is carried out.

The three serological methods that are currently being used in blood banks—indirect hemmagglutination (IHA), indirect immunofluorescence (IIF), and enzyme-linked immunosorbent assay (ELISA)—utilize mixtures of antigens prepared from the epimastigote form of the parasite. According to the World Health Organization (WHO), at least two positive tests of the three cited above are necessary for the diagnosis of the disease. Blood samples that are positive to only one of the three tests are classified as "indeterminate or inconclusive" and, in consequence, discarded. The indeterminate diagnosis is associated with 20 to 90% of all blood samples that gave one or more positive tests for Chagas' disease, depending on the methods employed and how they are applied. This high percentage of indeterminate results represents a serious problem in blood banks, both in terms of volume of discarded blood and doubtful diagnosis of Chagas' disease. In fact, a blood sample with a false positive test is no longer used for transfusion or isolation of cells and other blood components. Such loss of donated blood also affects the production of blood derivatives such as albumin, immunoglobulins and clotting factors which are of commercial value. Conversely, a blood sample with a false negative test is a dangerous source of contamination by the parasite.

The disadvantages of the current serological methods can be summarized as follows:
1. Low sensitivity: current methods use human sera at low dilutions, with a consequent increase in the background due to the cross-reactivity with natural antibodies and low-titer antibodies resulting from nonspecific polyclonal activation. Specific recombinant or synthetic epimastigote antigens, singly or in mixtures, are not sufficiently sensitive because they react only with a limited number of specific antibodies present in the sera of chronic Chagasic patient.
2. Low specificity: serological tests using epimastigote extracts cross-react with antigens from microbial sources other than *Trypanosoma cruzi*, notably Leishmania and some fungal and bacterial antigens.

BRIEF SUMMARY OF INVENTION

The invention describes the purification of the A&T and EpEx antigens, and their use in a chemiluminescent enzyme-linked immunosorbent assay (CL-ELISA), for the accurate diagnosis of Chagas' disease. When carried out in parallel, the results of the tests taken together provide high sensitivity and high specificity not obtainable with conventional methods described in the literature and/or which are commercially available.

BRIEF DESCRIPTION OF THE DRAWINGS

FIG. 1 describes the evaluation of the sensitivity of CL-ELISAs using A&T and EpEx antigens. Ch, chronic Chagas-disease patient sera (n=100); NHS, normal human sera or healthy blood-donor sera (n=200).

FIG. 2 describes the results of the CL-ELISA using A&T antigen as a criterion of cure of treated Chagasic patients. Parasitemia was estimated by either xenodiagnosis or hemoculture. Conventional diagnostic tests: indirect hemagglutination, indirect immunofluorescence, and ELISA. The Y-axis represents the serological titers for the assay, defined as the ratio of the test serum's value in relative luminescent units (RLU) to the cutoff value (titer=RLU/cutoff value).

DETAILED DESCRIPTION OF THE INVENTION

Purification of the A&T Antigen

A&T antigen is purified from trypomastigote forms of *Trypanosoma cruzi* according to Almeida et al., 1993 and Almeida et al., 1994a . Trypomastigote forms are obtained from infected green monkey kidney fibroblasts (LLC-MK$_2$ cells) cultured in Dulbecco's modified Eagle medium (D-MEM) containing 10% fetal bovine serum. The cell-derived trypomastigotes are collected 6–7 days later, following their release from infected cells, from the top fluid after sedimentation of the cell debris and incubation for 1.5 h at 37° C. Parasites are washed 3 times in 0.15 M phosphate-buffered saline (PBS), pH 7.4, centrifuged at 12,000 g, and kept at −70° C. until lyophilization. Lyophilized trypomastigotes are sequentially extracted 5 times with 10 volumes of chloroform/methanol (2:1), chloroform/methanol (1:2), chloroform/methanol/water (10:20:8), for 30 min each time, at room temperature. After centrifugation at 12,000 g, the organic extracts are discarded and the final delipidated pellet is dried under a stream of nitrogen. The dry pellet is then extracted 5 times with 10 volumes of 9% 1-butanol for 2 h each time, at room temperature. The soluble extract corresponds to the fraction containing at A&T antigen together with some hydrophilic and hydrophobic contaminants. The A&T-containing fraction is then lyophilized for 24 h and chromatographed on a column of octyl-Sepharose (Pharmacia-LKB, Upsala, Sweden), pre-equilibrated with 5% 1-propanol in 0.1 M ammonium acetate buffer, pH 7.2. The A&T-containing fraction dissolved in 5% 1-propanol in 0.1 M ammonium acetate buffer, pH 7.2 is applied to the column at a low flow rate. The colum is washed with 5% 1-propanol in 0.1 M ammonium acetate buffer, pH 7.2 and eluted with a 1-propanol gradient (5–60%). The column fractions containing the A&T antigen are tested for immunoreactivity with a specific polyclonal antibody generated against the A&T antigen (anti-A&T antibody). The A&T-positive fractions from the octyl-Sepharose column are pooled, dried and partitioned between water and 1-butanol. The aqueous phase is lyophilized for 24 h, resuspended in 5% 1-propanol in ammonium acetate 0.1 M, pH 7.2 and applied to the phenyl-Superose column (Pharmacia-LKB, Sweden) (pre-equilibrated with 5% 1-propanol in ammonium acetate 0.1 M, pH 7.2). The column is eluted with a 1-propanol gradient (5–60%). Material eluting in earlier fractions (column void) and containing the A&T antigen is pooled and lyophilized for 24 h. The material included in the column is basically constituted of hydrophobic contaminants, mainly phospholipids. Finally, as a final purification step to eliminate hydrophilic 3–2 contaminants, A&T antigenic preparation is re-applied to a column of octyl-Sepharose (Pharmacia-LKB, Sweden), pre-equilibrated with 5% 1-propanol in 0.1 M ammonium acetate buffer, pH 7.2. The A&T-containing fraction dissolved in 5% 1-propanol in 0.1 M ammonium acetate buffer, pH 7.2 is applied to the column at a low flow rate. The column is washed with 5% 1-propanol in 0.1 M ammonium acetate buffer, pH 7.2 and eluted with a 1-propanol gradient (5–70%) and eluted with a shallow I-propanol gradient (20–40%). The fractions are assayed for immunoreactivity with the anti-A&T antibody by dot-blotting and Western-blotting. Antibody binding fractions are pooled, exhaustively dialyzed against deionized water, lyophilized for 48 h, redissolved in deionized water and stored at −70° C.

Purification of the EpEx Antigen

EpEx antigen is prepared from epimastigote forms of *Trypanosoma cruzi*, Tulahuén strain. Parasites are cultured at 28° C., in Schneider's insect medium containing 20% fetal calf serum. After 7–10 days, the parasites are collected from the culture supernatant, washed three times with 100 mM phosphate-buffered saline, pH 7.4 and centrifuged at 12,000 g for 30 min, at 4° C. Pelleted parasites are immediately resuspended in 10 mM Tris-HCl buffer, pH 7.5, 0.2 mM leupeptin, 2 mM EDTA, 1% nonanoyl-N-methylglucamide (lysis buffer), and submitted to four cycles of freezing and thawing, in liquid nitrogen and water-bath (37° C.), respectively. The resulting lysate is centrifuged at 10,000 g for 5 min, at 4° C. The supernatant, containing the EpEx antigenic preparation, is removed and stored at −70° C.

Chemiluminescent Enzyme-linked Immunosorbent Assay (CL-ELISA) Using EpEx and A&T Antigens Chemiluminescent ELISA is carried out according to protocols previously described (Almeida et al., 1993, 1994b). A&T (at 0.15 µg dry weight/µl deionized water) and EpEx (at 0.15 µg.µl of lysis buffer) antigens are diluted in 50 mM sodium carbonate buffer, pH 9.6, for a final concentration of 0.2 ng/µl and 0.8 ng/µl, respectively. Fifty microliters of each antigen are separately added to wells of milky-white 96-well Maxisorp FluoroNunc plates (Nunc, Denmark). After 12 h at 4° C., plates are washed 5 times with 0.15 M phosphate-buffered saline, pH 7.4, 0.05% Tween 20 (PBS-T) and blocked with 0.1% bovine serum albumin (BSA) in 50 mM sodium carbonate buffer, pH 9.6, for 12 h at 4° C. or, alternatively, for 2 h at 37° C. Plates are then washed 5 times with 0.15 M phosphate-buffered saline, pH 7.4, 0.05% Tween 20 (PBS-T). The human sera, diluted 1:2,000 in PBS-T containing 0.5% BSA (PBS-TB), are added to the plates and incubated for 30 min at 37° C. Plates are washed 5 times with PBS-T, the excess liquid removed by inversion or filter paper, and then incubated with biotinylated goat anti-human IgG (Amersham, UK), diluted 1:2,000 with PBS-TB, for 30 min at 37° C. After washing 5 times with PBS-T, a streptavidin-horseradish peroxidase conjugate (Amersham, UK) diluted 1:1,000 with PBS-TB is added, following incubation for 30 rain at 37° C. Plates are washed 5 times with PBS-T, the excess liquid removed by inversion on filter paper, and then incubated with luminol (ECL reagents, Amersham, UK), diluted 1:20 in 50 mM carbonate buffer, pH 9.6, for 1–5 min at room temperature. Thereafter, the reaction is quantified using a luminometer for 96-well polysterene plate readings. The results are expressed as relative luminescent units (RLU). Cutoff values for A&T and EpEx CL-ELISAs were first calculated by determining the reactivities of 200 normal human sera (NHS). The mean and SD of these 200 reactivities were determined. A value of 10 times the SD was added to the mean for the cutoff value. The dispersion of the RLU readings for 200 NHS showed SD very close to the means using both A&T and EpEx CL-ELISAs (143±123 and 177±151, respectively). Therefore, for each plate in which a single negative control (pool of 100 NHS) in quadruplicate was included, the cutoff values for A&T and EpEx CL-ELISA were established as 10 times the negative control mean minus the background control mean (cutoff value=10×negative control mean–background control mean).

Result Interpretation

To interpret the results obtained, the luminometer reading of a serum sample is divided by the predeterminated cutoff value. A positive result is defined when the relative serum reading (RLU) is greater than 1, which represents the cutoff value. Conversely, a negative sample has an RLU equal or lower than 1.

1. The high sensitivity of the chemiluminescent (CL)-ELISA method permits the use of high dilutions of sera (1:2,000)

(FIG. 1), and thus eliminates most of the nonspecific or false-positive reactions of current methods, which use serum dilutions in the 1:30 to 1:400 range (Tables 1 and 2).

TABLE 1

Comparison between CL-ELISA (with A&T and EpEx) and conventional diagnostic tests with a panel of sera with inconclusive serology for Chagas' disease.

| Diagnostic test | Serum dilution | Number of sera | | | Number of sera | |
|---|---|---|---|---|---|---|
| | | Nega-tive | Incon-clusive | Posi-tive | False-Nega-tive | False-Posi-tive[1] |
| Chemilu-minescence | | | | | | |
| A&T-CL-ELISA[2] | 1:2,000 | 74 | 0 | 26 | 0 | 0 |
| EpEx-CL-ELISA | 1:2,000 | 72 | 0 | 28 | 0 | 2 |
| Western blotting-EpEx | 1:400 | 72 | 11 | 17 | 0 | 2 |
| ELISA-EpEx Commercial kits | 1:100 | 77 | 7 | 16 | 3 | 0 |
| ELISA-A1 | 1:41 | 10 | 70 | 20 | 0 | 64 |
| ELISA-A2 | 1:41 | 41 | 21 | 38 | 0 | 33 |
| ELISA-B | 1:41 | 67 | 8 | 25 | 0 | 7 |
| ELISA-C | 1:41 | 69 | 17 | 14 | 0 | 5 |
| HA | 1:40 | 79 | 12 | 9 | 5 | 0 |
| IF | 1:30 | 79 | 6 | 15 | 5 | 0 |

[1]No. Of false-positive sera = [no. Of positive + inconclusive sera with each test] – no. Of positive sera with the reference method (A&T-CL-ELISA).
[2]CL-ELISA with A&T antigen (CLE-A&T) is considered the gold method.

TABLE 2

CL-ELISA reactivity of A&T and EpEx antigens with inconclusive and heterologous sera.

| Conventional serology | Number of sera | Reactive sera in | | |
|---|---|---|---|---|
| | | Conventional tests[1] | CL-ELISA A&T | EpEx |
| Inconclusive for Chagas' disease | 100 | 100 | 26 | 28[2] |
| Leishmaniasis | | | | |
| visceral | 11 | 5 | 0 | 2 |
| cutaneous | 16 | 10 | 0 | 1 |
| AutoImmune diseases | 30 | 0 | 0 | 0 |
| Infectious diseases | | | | |
| AIDS | 24 | 0 | 0 | 0 |
| Hepatitis | 24 | 0 | 0 | 0 |
| Syphilis | 24 | 0 | 0 | 0 |
| Paracoccidioidomycosis | 5 | 1 | 0 | 0 |
| Poli A/C vaccinated (*Neisseria meningitidis*) | | | | |
| pre-immune | 5 | 0 | 0 | 0 |
| Immunized | 5 | 5 | 0 | 0 |
| Chagas' disease | 100 | 100 | 100 | 100 |
| Normal human sera | 200 | 0 | 0 | 0 |

[1]Number of sera giving at least 1 positive reaction in the conventional Chagas' disease serology (indirect immunofluorescence, indirect hemagglutination and ELISA).
[2]Two reactions with EpEx are false-positive.

2. The A&T antigen is a purified preparation of closely related molecules thar are specific of the trypomastigote stage obtained in tissue culture of mammalian cells, thus being very similar to the infective forms of the parasite that cause the disease in man.

3. Since the serological reactions with A&T antigen are highly specific, there is no cross-reactivity with antigens from a variety of other infectious agents including Leishmania, and with natural antibodies and low-titer antibodies resulting from nonspecific polyclonal activation (Table 2).

4. The A&T antigen is easily obtainable in amounts sufficient for a great number of tests in appropriate ELISA plates for chemiluminescent reading. Moreover, the purified A&T antigen is highly stable when fixed on plates for prolonged periods.

5. Since A&T antigen reacts with lytic (protective) antibodies, characteristic of active infection and present in high titers in chronic patient sera, it can be used to monitor the response of patients to chemotherapy (FIG. 2).

6. The EpEx complex antigen is prepared from the epimastigote form and contains many components that are also expressed in the infective stage. It reacts with antibodies that are recognized by conventional serology for Chagas' disease, but not with those antibodies whose reactions are due to artifacts such as blocking reagents, culture medium supplements, etc.

7. The EpEx antigen is readily prepared from fast growing epimastigote culture, and although it is not as specific as A&T purified antigen, it is highly sensitive and provide complementary and confirmatory data for the positive reactions obtained with A&T antigen (FIG. 1).

8. The advantages of using both A&T and EpEx antigens in parallel tests include the following:
   a) the antigens present in both tests are highly sensitive and therefore, a positive result with both antigens provides a diagnosis with a high level of confidence (FIG. 1, Table 1);
   b) positive reactivity with EpEx, and negative with A&T, while eliminating active Chagas' infection, suggests leishmaniasis or another infectious disease (Table 2);
   c) a decrease in the reactivity with A&T followed by a decrease with EpEx has prognostic value, and is a criterion of cure in patients submitted to chemotherapy (FIG. 2);
   d) when applied to sera classified as "indeterminate" (i.e. sera which are negative to one or two of the following tests: hemagglutination, immunofluorescence, and ELISA), the A&T and EpEx tests provide unambiguous results, thereby eliminating inconclusive serological diagnosis of Chagas' disease (Tables 1 and 2).

REFERENCES

World Health Organization (1991) Control of Chagas' disease. WHO *Tech. Rep. Ser.* 811:1–91

Hagar, J. M and Rahimtoola, S. H. (1991) Chagas' heart disease in the United States. *N. Engl. J. Med.* 325:763–8

Almeida, I. C., Krautz, G. M., Krettli, A. U. and Travassos, L. R. (1993) Glycoconjugates of *Trypanosoma cruzi*: a 74 kD antigen of trypomastigotes specifically reacts with lytic anti α galactosyl antibodies from patients with chronic Chagas disease. *J. Clin. Lab. Anal.* 7: 307–316.

Almeida, I. C., Ferguson, M. A. J., Schenkman, S. and Travassos, L. R. (1994a).Lytic anti-α-galactosyl antibodies from patients with chronic Chagas disease recognise novel O-linked oligosaccharides on mucin-like GPI-anchored glycoproteins of *Trypanosoma cruzi*. *Biochem. J.* 304: 793–802.

Almeida, I. C., Rodrigues, E. G. and Travassos, L. R. (1994b) Chemiluminescent immunoassays: discrimination between the reactivities of natural and human patient antibodies with antigens from eukaryotic pathogens, *Trypanosoma cruzi* and *Paracocidioides brasiliensis*. *J. Clin. Lab. Anal.* 8: 424–431.

What is claimed is:

1. A process for the preparation of Epimastigote Extract (EpEx) antigen from epimastigote forms of *T. Cruzi*, Tulahuén strain, which process comprises the steps of:

a) culturing the parasites thereof at a temperature of 28° C. in Schneider's insect culture medium containing 20% fetal calf serum, and after 7–10 days, b) collecting the parasites from the culture supernatant, c) washing the collected parasites 3–5 times with phosphate-buffered saline (PBS) at 100 mM at a pH of 7.3–7.4, d) centrifuging the washed parasites at 12,000–14,000 g for 30–45 minutes at 4–8° C., immediately thereafter e) resuspending the parasites in a tris(hydroxymethyl) aminomethane hydrochloride (Tris-HCl) buffer at 10 mM, pH of 7.4–7.5, containing 0.2–0.4 mM leupeptin, 2–3 mM ethylenediaminetetraacetic acid EDA, 1% nonanoyl-N-methylglucamide (lysis buffer), f) submitting the resuspended parasites to 4–6 cycles of freezing and thawing, in liquid nitrogen and in a water-bath at 37° C., respectively, g) centrifuging the resultant lysate at 10,000–12,000 g for 5–10 minutes, at 4–8° C., h) removing the supernatant containing the EpEx antigenic preparation, and i) storing the supernatant containing the EpEx antigenic preparation at −70° C. until use.

2. A test for the diagnosis of human Chagas' disease by a chemiluminescent enzyme-linked immunosorbent assay (CL-ELISA), using the EpEx antigen prepared according to claim 1 and Almeida & Travassos (A&T) antigen, which test comprises the steps of:

a) adding 40–100 nanograms of the EpEx antigen and 1–100 nanograms of the A&T antigen, both diluted in 50–100 mM carbonate-bicarbonate buffer with a pH of 9.4–9.6, separately, into wells of ELISA 96-well polystyrene test plates, b) incubating the antigens, and after 12–18 hours at 4–8° C., or 2–4 hours at 30–37° C., washing the plates 3–5 times with 0.15 mM phosphate-buffered saline (PBS) with a pH of 7.3–7.5 containing 0.05–0.1% Tween 20 (PBS-T Buffer), and subsequently blocking the free sites in the plates with 300 microliters of 0.1–0.2% bovine serum albumin (BSA) in 50–100 mM sodium carbonate-bicarbonate buffer with a pH of 9.4–9.6, for 12–24 hours at 4° C. or, alternatively, for 1–4 hours at 35–37° C., c) washing the plates 3–5 times with 300 ml of PBS-T buffer, and adding 50–100 microliters of the sera, diluted 1:2,000 in PBS-T buffer containing 0.1–0.5% BSA (PBS-TB buffer), into each well; incubating the diluted sera for 30 min. at 35–37° C., or 1 hour at 22–28° C., washing the plates with PBS-T, and removing the excess liquid by inversion on filter paper, d) adding 50–100 microliters of biotinylated anti-human IgG conjugate, diluted 1:2,000 in PBS-TB buffer into each well and incubating the plates for 5–30 min. at 35–37° C., or 1 hour at 22–28° C., and thereafter washing the plates washed 3–5 times with 300 microliters of PBS-T and removing excess liquid by inversion on filter paper, e) adding 50–100 microliters of streptavidin-horseradish peroxidase conjugate diluted 1:1,000–1:2,000 in PBS-T buffer into each well, incubating the plates for 30 min. at 35–37° C., or 1 hour at 22–28° C., washing the plates 3–5 times with 300 microliters of PBS-T buffer, and removing excess liquid by inversion on filter paper, f) incubating the plates for 5–30 min. at 22–28° C. with the chemiluminescent reagent 5-amino-2,3-dihydro-1, 4-phthalazinedione, diluted 1:10–1:20 in 50–100 mM carbonate-bicarbonate buffer, with a pH of 9.6–9.8 or, alternatively, diluted 1:5–1:10 in the same buffer containing 0.1–0.2% skimmed milk, and g) quantifying the luminescent reaction using a luminometer for 96-well microplate readings, and expressing the results as Relative Luminescent Units (RLU).

* * * * *